US012682996B2

(12) United States Patent
Austring et al.

(10) Patent No.: US 12,682,996 B2
(45) Date of Patent: *Jul. 14, 2026

(54) ELECTRONIC HEALTHCARE RECORD DATA BLOCKCHAIN SYSTEM AND PROCESS

(71) Applicant: Technologies IP, LLC, Fort Worth, TX (US)

(72) Inventors: Ronald Raymond Austring, English Harbour (AG); Kenneth A. Hill, Sr., Fort Worth, TX (US); Brad T. Crosslin, Keller, TX (US); Clinton S. Ferguson, III, Arlington, TX (US)

(73) Assignee: Technologies IP, LLC

( * ) Notice: Subject to any disclaimer, the term of this patent is extended or adjusted under 35 U.S.C. 154(b) by 0 days.

This patent is subject to a terminal disclaimer.

(21) Appl. No.: 19/044,337

(22) Filed: Feb. 3, 2025

(65) Prior Publication Data

US 2025/0182867 A1 Jun. 5, 2025

Related U.S. Application Data

(63) Continuation of application No. 18/595,305, filed on Mar. 4, 2024, now Pat. No. 12,217,840, which is a
(Continued)

(51) Int. Cl.
*G16H 10/60* (2018.01)
*G16H 20/10* (2018.01)
(Continued)

(52) U.S. Cl.
CPC ............ *G16H 10/60* (2018.01); *G16H 20/10* (2018.01); *H04L 9/0637* (2013.01); *H04L 9/50* (2022.05);
(Continued)

(58) Field of Classification Search
None
See application file for complete search history.

(56) References Cited

U.S. PATENT DOCUMENTS

| | | | |
|---|---|---|---|
| 8,917,165 B2 | 12/2014 | Marques | |
| 2002/0007284 A1 | 1/2002 | Schurenberg et al. | |

(Continued)

FOREIGN PATENT DOCUMENTS

| | | | | |
|---|---|---|---|---|
| WO | 2017027974 A1 | 2/2017 | | |
| WO | WO-2018064645 A1 * | 4/2018 | ............. | B33Y 50/02 |

(Continued)

OTHER PUBLICATIONS

Li, P., Nelson, S. D., Malin, B. A., & Chen, Y. (2019). DMMS: A decentralized blockchain ledger for the management of medication histories. Blockchain in Healthcare Today, 2, n/a. doi:http://dx.doi.org/10.30953/bhty.v2.38 (Year: 2019).*

(Continued)

*Primary Examiner* — Emily Huynh
(74) *Attorney, Agent, or Firm* — Enrique Sanchez, Jr.; Juan J Vasquez

(57) ABSTRACT

An Electronic Health Record (EHR) data blockchain system configured to allow multiple entities (e.g., pharmacy industry entities and healthcare providers that can act as data, service, product and service providers, and consumers) to connect to an EHR patient transaction blockchain (e.g., EHR-DATA-BC) and an EHR Data Patient Portal (e.g., EHR-Data-PP) to provide a centralized location for messages and subsequent edits to ensure uniform message data is presented. The EHR data blockchain system can include an EHR Data API, an EHR patient transaction blockchain API, and an EHR patient transaction blockchain. The EHR data blockchain system can provide workflow on the blockchain that can utilize smart contracts to define workflow processes, expected outcomes, and financial costs. When a
(Continued)

prescription transaction is complete, it will result in the settlement of each of the smart contracts that were added to the prescription workflow.

12 Claims, 2 Drawing Sheets

Related U.S. Application Data continuation of application No. 16/906,710, filed on Jun. 19, 2020, now Pat. No. 11,923,052.

(60) Provisional application No. 62/863,655, filed on Jun. 19, 2019, provisional application No. 62/863,637, filed on Jun. 19, 2019.

(51) Int. Cl.

| | |
|---|---|
| *H04L 9/00* | (2022.01) |
| *H04L 9/06* | (2006.01) |
| *G06Q 10/10* | (2023.01) |
| *G06Q 20/36* | (2012.01) |
| *G06Q 30/0207* | (2023.01) |

(52) U.S. Cl.
CPC ......... *G06Q 10/10* (2013.01); *G06Q 20/3678* (2013.01); *G06Q 30/0222* (2013.01); *G06Q 2220/00* (2013.01)

(56) References Cited

U.S. PATENT DOCUMENTS

| | | | |
|---|---|---|---|
| 2003/0005312 | A1 | 1/2003 | Sato |
| 2009/0208011 | A1 | 8/2009 | Ricciardi et al. |
| 2012/0323717 | A1 | 12/2012 | Kirsch |
| 2016/0117471 | A1 | 4/2016 | Belt |
| 2016/0335397 | A1 | 11/2016 | Blum |
| 2018/0117446 | A1 | 5/2018 | Tran et al. |
| 2018/0326291 | A1 | 11/2018 | Tran |
| 2019/0034924 | A1 | 1/2019 | Prabhu |
| 2019/0057763 | A1 | 2/2019 | Stockert et al. |
| 2019/0156938 | A1* | 5/2019 | Brunner ................. G16H 10/60 |
| 2019/0198144 | A1* | 6/2019 | Blackley ............... G16H 50/20 |
| 2019/0206536 | A1* | 7/2019 | Hausman ............. H04L 9/3247 |
| 2019/0303610 | A1* | 10/2019 | Bodegas Martinez ...................... G06F 16/152 |
| 2020/0057867 | A1* | 2/2020 | Aunger ............... H04L 63/0428 |
| 2020/0402624 | A1 | 12/2020 | Austring |
| 2020/0402629 | A1 | 12/2020 | Austring |
| 2021/0004990 | A1 | 1/2021 | Lee |
| 2022/0092566 | A1 | 3/2022 | Austring |
| 2022/0093225 | A1 | 3/2022 | Austring |

FOREIGN PATENT DOCUMENTS

| | | |
|---|---|---|
| WO | 2018152410 A1 | 8/2018 |
| WO | 2019083897 A1 | 5/2019 |
| WO | 2020041528 A1 | 2/2020 |

OTHER PUBLICATIONS

Shrier et al., Blockchain and Health IT: Algorithms, Privacy, and Data—Whitepaper, Aug. 8, 2016, pp. 74-84.

Li, et al. (2019). DMMS: A decentralized blockchain ledger for the management of medication histories, Blockchain in Healthcare today, 2, n/z. doi:http://dx.doi.org/10.30953/hty.v2.38 (Year: 2019).

Samsi, et al., A Mechanism for Privacy Preserving in Healthcare Organizations, pp. 208-213, Faculty of Computing, Universiti Teknologi Malaysia, 2014.

* cited by examiner

ELECTRONIC HEALTHCARE RECORD DATA BLOCKCHAIN SYSTEM AND PROCESS

CROSS REFERENCE TO RELATED APPLICATIONS

The present application is a Continuation application of U.S. patent application Ser. No. 18/595,305, filed Mar. 4, 2024, which is a Continuation application of U.S. patent application Ser. No. 16/906,710, filed Jun. 19, 2020, which claims priority to U.S. Provisional Application Ser. No. 62/863,637, filed on Jun. 19, 2019, and entitled "Electronic Health Record Data Blockchain System and Process," and U.S. Provisional Application Ser. No. 62/863,655, filed on Jun. 19, 2019, and entitled "Electronic Health Record Data Blockchain System," the entirety of both applications are incorporated herein by reference.

TECHNICAL FIELD

The present disclosure generally relates to blockchain-enabled patient data systems, and more specifically to blockchain-enabled patient data systems configured to facilitate anonymous patient data transactions between multiple entities.

BACKGROUND

The healthcare industry today is comprised of "Centralized" and "Decentralized" (based on hubs) network structures and multiple independent data silos. In traditional electronic patient record systems, systems are configured according to the conventional client-server model, where a message is sent to a server and the server send a response, according to standards promulgated by the National Council for Prescription Drug Programs (NCPDP). Many times, the client and the server can have inapposite databases, such as Oracle® and MS SQL® databases. Additionally, each message sent and received is recorded by the client and the server. Often times, discrepancies can arise between the client and the server regarding the actual contents of the messages due to latency, dropped packets, and other various system issues.

In particular pharmacy patient information messages can be edited by multiple entities as they make their way from a pharmacy to a payer for payment. As each entity in the chain edits the message, additional complexities are added that can result in additional message discrepancies, including incompatible data tagging, data formatting, authentication, etc. This can result in multiple databases with a message with varying message integrities. Such discrepancies result in wasted effort, time, and money directed toward resolution of the discrepancies.

Further, the availability of patient-identifiable data stored in databases invites the possibility of HIPPA violations and incorrect handling of data. Multiple systems may be required to monitor prescriptions, provide edits, provide offers, determine drug eligibility, identify fulfilment options, and finalize pricing, wasting precious resources, adding complexity, and resulting in excess costs.

SUMMARY

The present disclosure teaches technical advantages as an Electronic Health Record (EHR) data blockchain system configured to allow multiple entities (e.g., pharmacy industry entities that can act as data, service, product providers, and consumers) to connect to an EHR patient transaction blockchain (e.g., EHR-DATA-BC) and an EHR Data Patient Portal (e.g., EHR-Data-PP) to provide a centralized location for patient information messages and subsequent edits to ensure uniform message data.

The present disclosure solves the technological problem of mitigating data discrepancies for electronic patient data, implemented over multiple systems. Additionally, the present disclosure overcomes issues related to the multiple transfers of patient identifiable information (PII). Further, the present disclosure solved the problems associated with transaction funding and incentivizing.

In particular, the present disclosure improves the performance of traditional systems by implementing an EHR data blockchain system (including an EHR Data API, an EHR patient transaction blockchain API, and an EHR patient transaction blockchain) that can provide a centralized patient transaction processing location that creates transparency, immutable verification, interactive transaction editing, and digital currency transactions (e.g., cryptocurrency transactions to occur using each parties' digital wallet information). The EHR Data API can access and retrieve patient identifiable information (PII) and generate a non-patient-identifiable Single Purpose Patient ID (SPPID) for a particular patient. The EHR patient transaction blockchain API (e.g., EHR-DATA-BC-API) can be configured to store the SPPID, as well as particular, discrete data retrieved from the EHR for a patient, execute smart contracts, and control the execution of digital currency transfers, among other functions.

The disclosed system maintains the integrity and privacy of patient information and reduces the discrepancies in the data, while simplifying the system architecture. A patient's private information, including the patient's name, address, phone number, social security number, insurance information, medical history, clinical information, and other relevant information, can be stored in an Electronic Health Record (EHR) database, such as an Electronic Patient Outcome Record (EPOR), Solid POD, XML file, or other suitable data storage element. Advantageously, no patient identifiable information will be stored in the EHR patient transaction blockchain in order to assure the anonymity of the patient data. Instead, when a new blockchain transaction is initiated by an entity for a particular patient, the EHR database can be queried to determine if the patient already has a record in the database. If the patient has a record in the EHR database, a Single Purpose Patient ID (SPPID) can be generated and returned to the requesting entity. The SPPID can be used instead of patient identifiable information. The SPPID can be used only until the transaction is completed. The next time a blockchain transaction related to the patient is submitted, the patient will be issued a new SPPID, thereby ensuring that an SPPID is not indefinitely associated with the patient.

The EHR patient transaction blockchain can be used as a workflow space to process the transaction until the transaction is completed, signed, distributed for consensus, and funded. Smart contracts can be implemented to define workflow processes, drug interactions, fulfillment, expected outcomes, triggering events, and pricing, among others. Multiomics can tailor drugs to fit a patient's complex human structure and can deliver better patient outcomes. The present disclosure can facilitate real-time data collection from a variety of devices monitoring our bodies to advance and accelerate drug research. Optimal use of this data will require collection before, during and after drug therapy. Data queries, designed for drug research, can cross reference this data with the actual prescribed usage of the drugs, resulting in an extremely valuable feedback loop to the manufacturer.

Among its embodiments, the present disclosure teaches a "Distributed" model with one healthcare data silo. The single silo "Distributed" model can be built using Distributed Ledger Technology (DLT), will be immutable, and easily accessible to all stakeholders. A DLT known as blockchain technology can be used to record and distribute, electronic prescriptions, prescription transactions, clinical transactions, pharmacy systems workflow, healthcare provider transactions, and medical device data. The initial network structure can include various nodes, located in various locations, designed to provide maximum throughput for distributed applications connected to the network. By recording all prescription transactions on the blockchain and providing an API for state and federal government agencies, government and law enforcement agencies can have a national view of all prescription data.

Pharmacy workflow steps and processes are contained within individual pharmacy systems. The EHR Data blockchain system can moves these steps and processes to the blockchain, which can allow: prescription filling applications to be more efficient; the rapid adoption of new technologies, algorithms, edits, services; and provides a new method of interaction among stakeholders. The EHR data blockchain system can provide workflow on the blockchain that can utilize smart contracts to define workflow processes, expected outcomes, and financial costs. When a prescription transaction is complete, it will result in the settlement of each of the smart contracts that were added to the prescription workflow. Settlement will determine if the smart contract was utilized during prescription filling and may result in the exchange of digital currency (e.g., EHRCash™, Bitcoin®, etc.), utility tokens, vouchers, or other suitable notes, between the parties involved in the smart contract. For example, the exchange of EHRCash™ tokens can be immediate (sub-millisecond delay) and can eliminate the need for standard accounting processes (i.e. invoicing, statements, accounts receivable and accounts payable) in order to collect money from trading partners.

All entities can directly communicate with the EHR patient transaction blockchain through a predefined blockchain application programming interface (e.g., EHR-Data-BC-API). The system can facilitate the transfer of anonymous patient data between multiple entities, including:

Physicians
Pharmacies
  Independent
  Chain
  Central Fill
  Mail Order
Drug Manufacturers
Drug Wholesalers
Prescription editing providers
  Drug Utilization Review
  Genomic
  Pricing
Prescription Benefit Managers.
Pharmacy Software Vendors
National Facilitators
Shipping Services (Federal Express, DHL, etc.)
Delivery Services
Prescription Call Centers
Government Agencies
Others It is an object of the disclosure to provide an electronic health record data blockchain system configured to process a prescription transaction for a patient. It is a further object of the disclosure to provide a method of providing blockchain-based electronic health record data patient transactions, the method implemented by a server system comprising one or more processors executing computer program instructions that, when executed, perform the method. It is a further object of the disclosure to provide an electronic health record data blockchain system configured to process a prescription transaction for a patient. These and other objects are provided by the following embodiments.

In one exemplary embodiment, an electronic health record data blockchain system configured to process a prescription transaction for a patient, can include: one or more computer-readable storage media configured to store a blockchain; a computer system comprising one or more processors programmed to execute computer program instructions that, when executed, cause the computer system to: generate a single-purpose patient ID (SPPID) for a patient; receive an electronic prescription having a plurality of parameters from an electronic medical record system; initiate a new prescription transaction for the patient on the blockchain using the prescription, the SPPID, and no patient-identifying information; receive a prescription transaction edit from one or more providers; generate a smart contract configured to edit at least one of the plurality of prescription parameters and write an edit record to the blockchain; generate a close record based on the edit record, the close record indicating a drug and a price to be paid and write the close record to the blockchain; and initiate one or more digital currency transactions related to the prescription transaction once the close record has been written to the blockchain.

In another exemplary embodiment, a method of providing blockchain-based electronic health record data patient transactions, the method implemented by a server system comprising one or more processors executing computer program instructions that, when executed, perform the method, can include: generating a single-purpose patient ID (SPPID) for a patient; receiving an electronic prescription having a plurality of parameters from an electronic medical record system; initiating a new prescription transaction for the patient on the blockchain using the prescription, the SPPID, and no patient-identifying information; receiving a prescription transaction edit from one or more providers; generating a smart contract configured to edit at least one of the plurality of prescription parameters and write an edit record to the blockchain; generating a close record based on the edit record, the close record indicating a drug and a price to be paid and write the close record to the blockchain; and initiating one or more digital currency transactions related to the prescription transaction once the close record has been written to the blockchain.

In another exemplary embodiment, an electronic health record data blockchain system configured to process a prescription transaction for a patient, can include: one or more computer-readable storage media configured to store a blockchain; and a computer system comprising one or more processors programmed to execute computer program instructions to make one or more edits to a prescription transaction stored on the blockchain, including: an EHR application programming interface (API) configured to access and retrieve patient identifiable information (PII) and generate a non-patient-identifiable Single Purpose Patient ID (SPPID) for a patient, and a blockchain API configured to store the SPPID and non-patient-identifying information related to the patient transaction on the blockchain, edit the prescription transaction on the blockchain, execute smart contracts related to the prescription transaction on the blockchain, and control the execution of digital currency transfers related to the prescription transaction on the blockchain.

DETAILED DESCRIPTION

The preferred version of the disclosure presented in the following written description and the various features and advantageous details thereof, are explained more fully with reference to the non-limiting examples included in the accompanying drawings and as detailed in the description, which follows. Descriptions of well-known components have been omitted so to not unnecessarily obscure the principle features described herein. The examples used in the following description are intended to facilitate an understanding of the ways in which the disclosure can be implemented and practiced. Accordingly, these examples should not be construed as limiting the scope of the claims.

Figure 1:
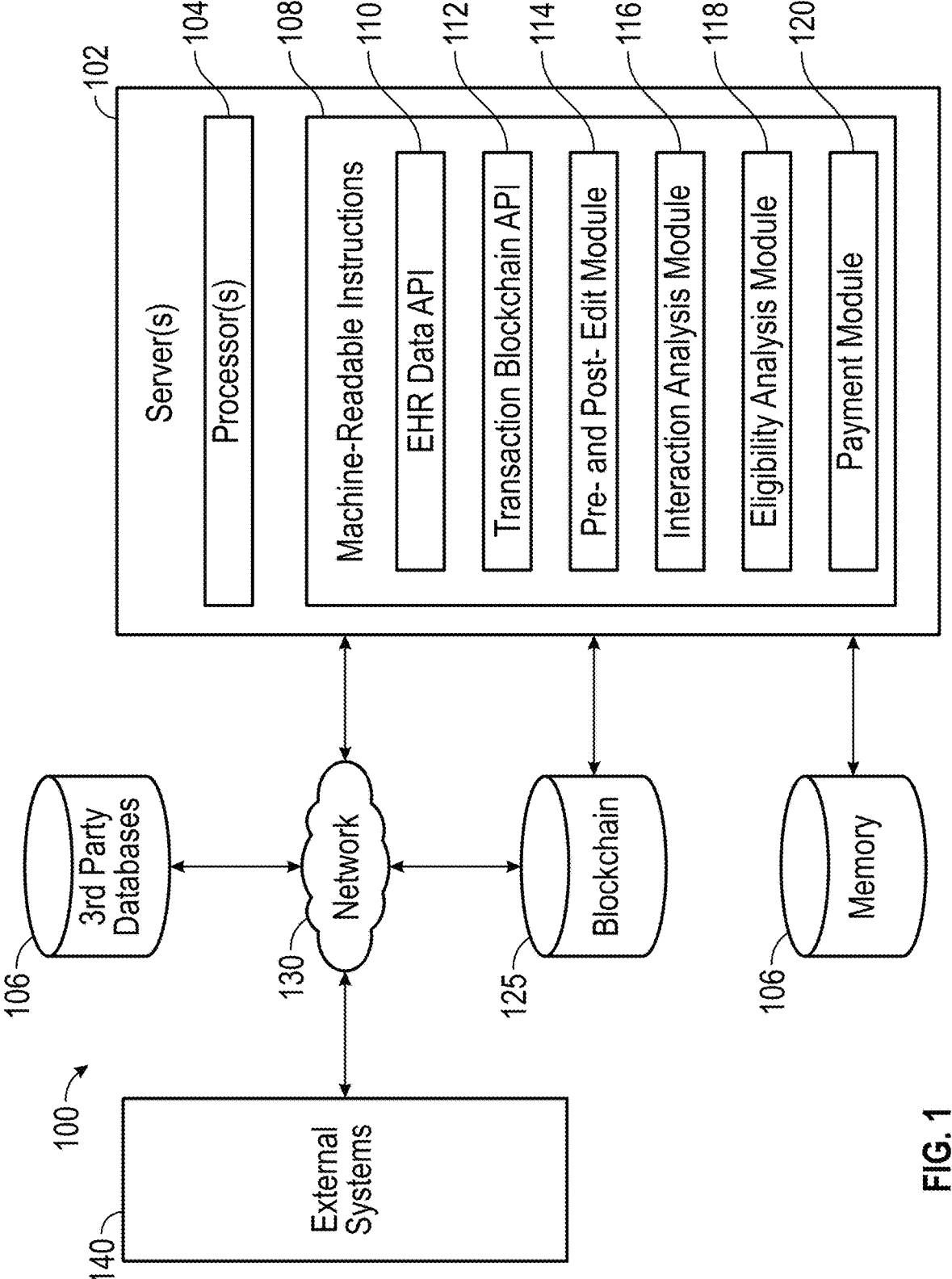
FIG. 1 shows a schematic view of an electronic health record data blockchain system, in accordance with one or more exemplary embodiments of the present disclosure.

FIG. 1 shows a schematic view of an electronic health record data blockchain system, in accordance with one or more exemplary embodiments of the present disclosure. The EHR-DATA-BC system 100 can include a server 102, third party databases 106, a distributed ledger 125, a network 130, and external systems 140.

The server 102 can include one or more processors (or cores) 104, a memory 106, and machine-readable instructions 108. In one exemplary embodiment, the machine-readable instructions 108 can include an EHR Data API 110, a transaction blockchain API 112, a pre- and post-edit module 114, an interaction analysis module 116, an eligibility analysis module 118, and a payment module 120. Additionally, the server 102 can host an EHR Data Patient Portal (EHR-Data-PP) that can provide a patient with access to the system 100 after an authenticated login. The server 102 can be implemented in hardware, software, or a suitable combination of hardware and software therefor, and may comprise one or more software systems operating on one or more servers, having one or more processors, with access to memory. Server(s) can include electronic storage, one or more processors, and/or other components. Server(s) can include communication lines, or ports to enable the exchange of information with a network and/or other computing platforms. Server(s) can also include a plurality of hardware, software, and/or firmware components operating together to provide the functionality attributed herein to server(s). For example, server(s) can be implemented by a cloud of computing platforms operating together as server(s). Additionally, the server can include memory 106.

Server(s) can include electronic storage, one or more processors, and/or other components. Server(s) can include communication lines, or ports to enable the exchange of information with a network and/or other computing platforms. Server(s) can also include a plurality of hardware, software, and/or firmware components operating together to provide the functionality attributed herein to server(s). For example, server(s) can be implemented by a cloud of computing platforms operating together as server(s).

Memory 106 can comprise electronic storage that can include non-transitory storage media that electronically stores information. The electronic storage media of electronic storage May include one or both of system storage that can be provided integrally (i.e., substantially non-removable) with server(s) and/or removable storage that can be removably connectable to server(s) via, for example, a port (e.g., a USB port, a firewire port, etc.) or a drive (e.g., a disk drive, etc.). Electronic storage may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage can include one or more virtual storage resources (e.g., cloud storage, a virtual private network, and/or other virtual storage resources). Electronic storage can store machine-readable instructions, software algorithms, information determined by processor(s), information received from server(s), information received from computing platform(s), and/or other information that enables server(s) to function as described herein. The electronic storage can also be accessible via a network connection.

Processor(s) 104 can be configured to provide information processing capabilities in server(s). As such, processor(s) can include one or more of a digital processor, an analog processor, a digital circuit designed to process information, an analog circuit designed to process information, a state machine, and/or other mechanisms for electronically processing information, such as FPGAs or ASICs. The processor(s) can be a single entity or include a plurality of processing units. These processing units can be physically located within the same device or represent the processing functionality of a plurality of devices operating in coordination or software functionality.

The processor(s) 104 can be configured to execute machine-readable instructions 108 or learning modules by software, hardware, firmware, some combination of software, hardware, firmware, and/or other mechanisms for configuring processing capabilities on processor(s). As used herein, the term "machine-readable instruction" may refer to any component or set of components that perform the functionality attributed to the machine-readable instruction component. This can include one or more physical processors during execution of processor readable instructions, the processor readable instructions, circuitry, hardware, storage media, or any other components.

The server 102 can be configured with machine-readable instructions 108 having one or more functional modules. The machine-readable instructions can be implemented on one or more servers, having one or more processors, with access to memory. The machine-readable instructions can be a single networked node, or a machine cluster, which can include a distributed architecture of a plurality of networked nodes. The machine-readable instructions can include control logic for implementing various functionality, as described in more detail below. The machine-readable instructions can include certain functionality associated with an EHR Data Patient Portal (EHR-Data-PP), EHR Data API (first server-side computer system) 110, EHR patient transaction blockchain API (second server-side computer system), pre- and post-edit module 114, interaction analysis module 116, eligibility analysis module 118, and payment module 120. External databases and external systems 140, as well as an EHR Data Blockchain client (client computer system) can also be implemented on one or more servers 102, having one or more processors 104, with access to memory 106.

In one exemplary embodiment, the EHR Data API 110 can provide an interface that defines interactions between multiple software components. For example, EHR Data API 110 can define the kinds of calls or requests that can be made, how to make them, the data formats that should be used, the conventions to follow, and other suitable functionality. In another exemplary embodiment, the EHR Data API 110 can access and retrieve patient identifiable information (PII) and generate a non-patient-identifiable Single Purpose Patient ID (SPPID) for a particular patient.

In one exemplary embodiment, the EHR patient transaction blockchain API 112 (e.g., EHR-DATA-BC-API) can provide an interface that defines interactions between multiple software components. For example, EHR patient transaction blockchain API 112 can define the kinds of calls or requests that can be made, how to make them, the data formats that should be used, the conventions to follow, and other suitable functionality. In another exemplary embodiment, the transaction blockchain API 112 can be configured to store the SPPID, as well as particular, discrete data retrieved from the EHR for a patient, execute smart contracts, and control the execution of digital currency transfers, among other functions.

In one exemplary embodiment, a pre- and post-edit module 114 can edit received distributed ledger transactions according to input received from eternal systems 140, third-party databases 106, or other suitable systems. In another exemplary embodiment, the transactions can be processed in real-time while a pharmacy is filling a prescription. For example, "pre-edit" and post-edit" processing can be used by pharmacies and payers in the industry to examine prescription claims for accuracy and consistency using predetermined data and rules for processing claims. In another exemplary embodiment, the pre- and post-edit module 114 can analyze the patient clinical data in the context of the submitted prescription and information about the prescribed pharmaceuticals and complete the pre-editing process. For example, the module 114 can receive patient clinical data from third party databases 106 and correlate the prescription information with the patient clinical data to determine whether the incorrect dosage or timing is prescribed, given the patient's height, weight, or other patient factors. In another exemplary embodiment, the EHR Data API 110 can be operably coupled to the pre- and post-edit module 114 to provide relevant patient information related to the transaction to the pre- and post-edit module 114. In another exemplary embodiment, the EHR patient transaction blockchain API 112 can be operably coupled to the pre- and post-edit module 114 to store the particular, discrete data retrieved from the EHR for a patient related to the transaction.

In one exemplary embodiment, an interaction analysis module 116 can receive information related to potential drug interactions and read and write that data to the distributed ledger 125. For example, the interaction analysis module 116 can analyze transaction information with patient clinical data extracted from the third-party databases 106, including at least one or more of information about potential drug interactions with other drugs and patient risk factors, including information selected from the group consisting of patient laboratory data, genomic data, immunizations, and allergies. In one exemplary embodiment, an eligibility analysis module 118 can make patient eligibility determinations related to the transaction. For example, the eligibility analysis module 118 can receive a patient's insurance information and correlate that information with the transaction data to determine eligibility for discounts, and other relevant content.

In one exemplary embodiment, the payment module 120 can determine if a smart contract was utilized during prescription filling and may result in the exchange of digital currency (e.g., EHRCash™, Bitcoin®, etc.), utility tokens, vouchers, or other suitable notes, between the parties involved in the smart contract. For example, the exchange of EHRCash™ tokens can be immediate (sub-millisecond delay) and can eliminate the need for standard accounting processes (i.e. invoicing, statements, accounts receivable and accounts payable) in order to collect money from trading partners. In another exemplary embodiment, the payment module 120 can utilize stored digital wallet information to effect the digital currency transactions. The modules described herein can be executed, called, or otherwise implemented via server, control logic, API, or other suitable means.

The distributed ledger 125 can be one or more EHR Data blockchains implemented on one or more platforms, including BigChainDB, nChain, Ethereum, Hyperledger, R3, Ripple, EOS, or other suitable blockchain platform. The EHR Data blockchain can be a public blockchain, accessible to the general public, or a private blockchain, accessible only by those parties credentialed for access.

The aforementioned system components, APIs, and modules, can be communicably coupled to each other via the Internet, intranet, system bus, or other suitable network 130. The communication can be encrypted, unencrypted, over a VPN tunnel, or other suitable communication means. The network 130 can be a WAN, LAN, PAN, or other suitable network. The network communication between the system components 102, 104, 106, 108, 110, and 112, can be encrypted using PGP, Blowfish, AES, 3DES, HTTPS, or other suitable encryption. The network communication can occur via application programming interface (API), health level 7 (HL7) standard, ANSI-X12, Ethernet, PCI, PCIe, InfiniBand, Wi-Fi, Bluetooth, or other suitable communication protocol.

Third party databases 106 can be operably coupled to the system components via the network 130. In one exemplary embodiment, the third-party databases 106 can include an electronic medical record system (EMR), an Electronic Patient Outcome Record (EPOR) database, pharmacy databases, a plurality of patient databases, a clinical database, a genomic database, a laboratory database, a disease database, a standardized drug database, a research database, and other suitable databases. In another exemplary embodiment, the third-party databases can function as archival nodes. The archival nodes can keep a real-time (sub-millisecond) encrypted copy of the distributed ledger 125. The archival node can provide fault tolerance and makes the contents of the distributed ledger 125 readily available to a host so that additional data processing, reporting, and analytics can be achieved. Instead of having to traverse the EHR Data API 110, the host can query its own machines to acquire the data. Any third party can host a drug archival node. In another exemplary embodiment, the archival node can provide data restoration to the distributed ledger 125. In another exemplary embodiment, the archival node can keep the older distributed ledger data accessible in a non-production system, so that the production distributed ledger can direct its full capabilities toward current transactions. In another exemplary embodiment, the distributed ledger can be transferred to the archival node once a distributed ledger transaction closes.

External systems 140 can be operably coupled to the system components via the network 130. External systems 140 can include patient devices, pharmacy devices, payer devices, financial institution devices, insurance devices, medical devices, IoT devices, or other suitable systems or devices. Such systems and devices can include smart phones, tablets, wearable devices, laptops, desktops, servers, appliances, or other suitable devices. In one exemplary embodiment, an external system 140 can be EHR-Data-BC-Client.

Figure 2:
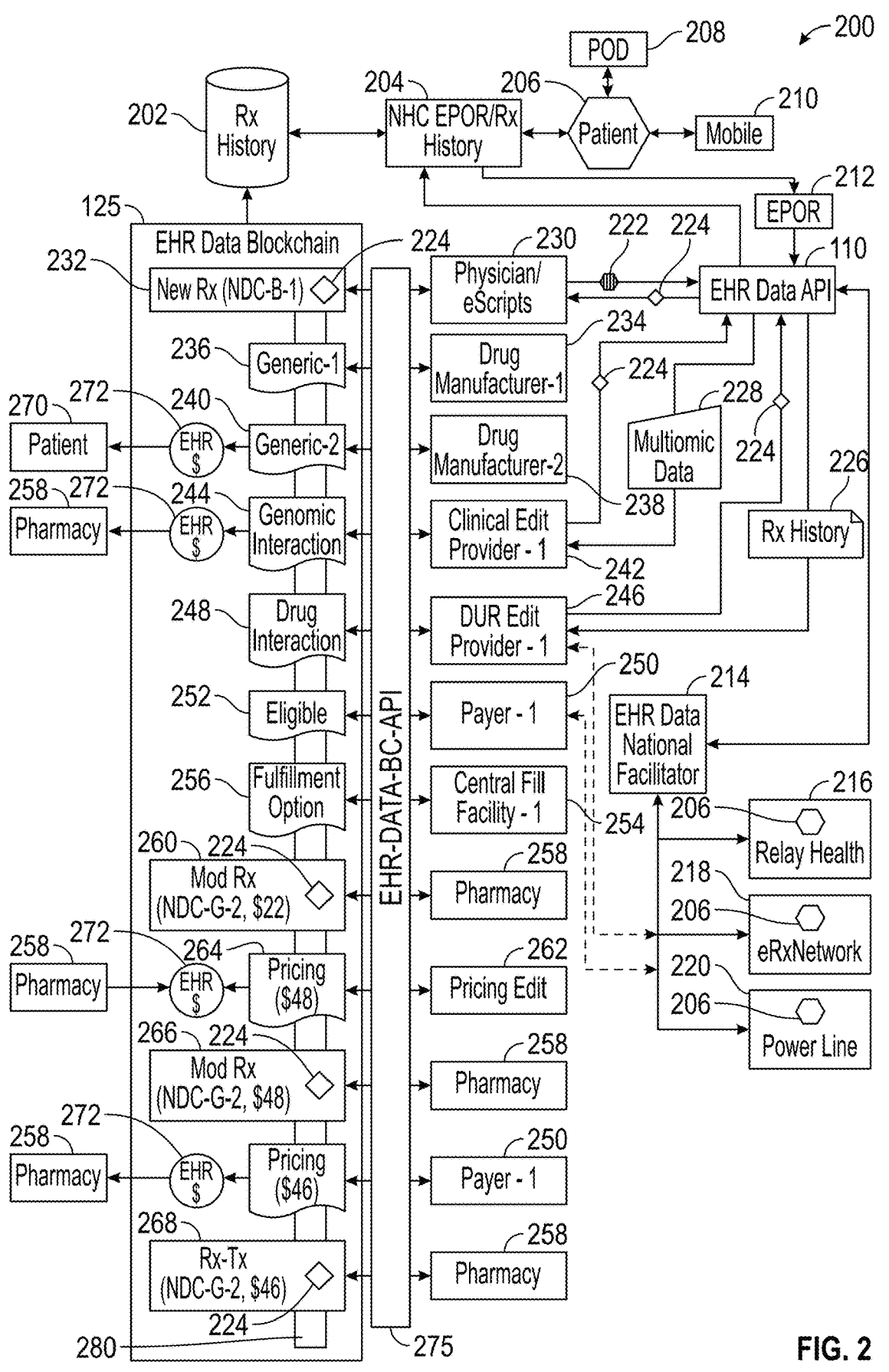
FIG. 2 shows a schematic view of an electronic health record data blockchain system transaction, in accordance with one or more exemplary embodiments of the present disclosure.

FIG. 2 shows a schematic view of an electronic health record data blockchain system transaction, in accordance with one or more exemplary embodiments of the present disclosure. The EHR data blockchain system 200 can include and an Electronic Health Record (EHR) system 204 including electronic health records 226 for a plurality of patients stored in an EHR database 202, with patient identifying information 206. In one exemplary embodiment, each EHR can include a patient's contact information, height weight, age, blood type, prescription history, multi-omic data, clinical history, patient outcome data, insurance information, account information, and other relevant information related to the patient. Additionally, the EHR can include information from mobile devices 210 related to the user, as well as wearable devices related to the user.

The EHR system data can be accessed via an EHR Data Application Programming Interface (API) 110. The EHR Data API 110 can be operably coupled to one or more electronic health record data providers, such as an Electronic Patient Outcome Record (EPOR) system 212, a national facilitator 214, or other health network. In one exemplary embodiment, the EHR Data API 110 can query databases, retrieve requested information, write data to a database, and modify data, among other functions. The EHR Data API 110 can run on a server, stand-alone computer, appliance, software-as-a-service (SaaS), platform-as-a-service (PaaS), or other suitable device.

To further illustrate the EHR data blockchain system 200 functionality and capability, exemplary embodiments will be presented below related to a pharmacy transaction. However, the EHR data blockchain system 200 is not, and should not be, limited to pharmacy transactions. Any healthcare transaction requiring patient data is contemplated by the EHR data blockchain system disclosed herein.

In one exemplary embodiment, a physician can enter a prescription for a patient into a client computer system, such as eScripts® or other suitable Electronic Medical Record (EMR) system 230, that can initiate a blockchain transaction 280. The prescription can be subject to pre- and post-edits 114, interaction analysis 116, eligibility analysis 118, and final payment 120.

In one exemplary embodiment, a physician through a client computer system, such as eScripts® or other suitable Electronic Medical Record (EMR) 230, can write a prescription for a particular patient. The physician, through the client computer system 230, can send a patient look up query 222 to the EHR Data API 110, to determine whether the EHR system 204 has any information related to the particular patient. The client computer system 230 can send a query 222 with patient identifying information, such as the patient's name, phone number, address, Social Security number, or other suitable information, to the EHR Data API 110. The EHR Data API 110 can then query the EHR system 204 to identify whether the EHR system 204 includes an EHR 226 for the specified patient.

In another exemplary embodiment, if the EHR system 204 includes a record 226 for the specified patient, the EHR Data API 110 can return a single purpose patient ID (SPPID) 224 to the client computer system. The SPPID 224 can be used instead of patient identifiable information to ensure patient privacy. In another exemplary embodiment, the SPPID 224 can be used only until the transaction 280 is completed. The next time a blockchain transaction 280 related to the patient is submitted, the patient can be issued a new SPPID 224, thereby ensuring that an SPPID 224 is not indefinitely associated with the patient for all future transactions. This process can ensure that even if a single SPPID 224 is compromised, such that a patient's identifiable information (PII) 206 can be determined, the compromise will be limited to a single transaction. In another exemplary embodiment, anonymity can be promulgated through a Single Purpose Pharmacy ID (SPPhaID) that can be utilized as a unique identifier to protect the identity of the specific pharmacy for the transaction, a Single Purpose Physician ID (SPPhyID) that can be utilized as a unique identifier to protect the identity of a specific physician for the transaction, and a Single Purpose Payer ID (SPPayID) that can be utilized as a unique identifier to protect the identity of the specific payer for the transaction.

In one exemplary embodiment, once a transaction 280 is completed, the SPPID 224 can only be used to read information, associated with the transaction, from the blockchain 125. In another exemplary embodiment, based on permissions granted by the patient, EHR system 204 can group the transaction data, with other transactions, medical device data, etc., associated with the patient, for reporting, analytics, drug research, etc. For example, a drug company may wish to understand how a specific drug effects patient heart rates. A report can be sent to the drug manufacturer or application 234, 238 from EHR system 204 including all a patient's transactions for the specified drug, along with heart rate data from a user device 210 accumulated for the patient while the patient was taking the specified drug. In its raw form an SPPID 224 can have a predetermined size (e.g., 256 bits), but this value can be hashed to a different size by the EHR Data API 110.

In one exemplary embodiment, the physician, via the client computer system 230, can write a blockchain record to the blockchain 125, via an EHR Data Blockchain API 275 (e.g., EHR-Data-BC-API), to initiate a blockchain prescription transaction 280. The blockchain record can include all of the data in a traditional prescription, including the drug name, the dosage, the administration period, among others. In another exemplary embodiment, the EHR Data Blockchain API 275 can generate a notification to notify drug manufactures 234, 238 of the new blockchain prescription transaction 280 to allow the drug manufacturers 234, 238 to offer alternatives to the drug identified in the blockchain transaction record 232, alternatives that satisfy the same therapeutic needs as the indicated drug, by writing a record with the alternative drug information 236 to the blockchain 125, via the EHR Data Blockchain API 275. The drug manufacturers 234, 238 can communicate with the EHR Blockchain API 275 using a client computer system, manufacturer portal, or other suitable communication means. In another exemplary embodiment, one or more drug manufacturers 234, 238 can write a record to the blockchain prescription transaction 280. The record 232 can be a ledger entry, smart contract, text file, or other suitable data container. Because of the use of the SPPID 224, the competing drug manufacturers 234, 238 have no patient identifying information 206, so the transaction runs no risk of violating Health Insurance Portability and Accountability Act (HIPAA) regulations, even if placed on a public blockchain.

In one exemplary embodiment, a clinical edit provider or application 242 can be notified by the EHR Data Blockchain API 275 of a new transaction 280, such as a prescription transaction. In another exemplary embodiment, the clinical edit provider 242 can retrieve the SPPID 224 and the prescribed drug information from the blockchain prescription record 232, send the SPPID 224 to the EHR Data API 110 to retrieve the specific patient's multiomic data, and determine whether any changes need to be made to the prescription using the interaction analysis module 114 or other suitable software. The clinical edit provider 242 can retrieve any available EHR information for the specific patient (including genomic data, metabolic data, etc.) through the EHR Data API 110, to determine the suitability of the prescription for the specific patient. In another exemplary embodiment, the clinical edit provider 242 can write a genomic interaction record 244 to the blockchain prescription transaction 280, through the EHR Blockchain API 275, editing the prescription accordingly, via pre- and post-edit module 114, or other suitable software. The record 244 can be a smart contract that executes, given certain conditions, to effect a specific outcome, such as editing of the prescription record 232 pursuant to the specific patient genomic interaction determination.

In one exemplary embodiment, a DUR edit provider or application 246 can be notified by the EHR Blockchain API 275 of a new transaction 280, such as a prescription transaction. The DUR edit provider 246 can retrieve the SPPID 224 and the prescribed drug information from the blockchain prescription record 232, send the SPPID 224 to the EHR Data API 110 to retrieve the specific patient's prescription history data, and determine whether any drug interactions exist such that changes need to be made to the prescription. In another exemplary embodiment, the DUR edit provider 246 can retrieve any available EHR information for the specific patient (including allergy data, metabolic data, previous reaction data, active drugs being taken, etc.) through the EHR Data API 110, to determine the suitability of the prescription for the specific patient. The DUR edit provider 246 can write a drug interaction record 248 to the blockchain prescription transaction 280, through the EHR Blockchain API 275, editing the prescription accordingly. Additionally, this record 248 can be a smart contract that executes, given certain conditions, to effect a specific outcome, such as editing of the prescription pursuant to the drug interaction determination.

In one exemplary embodiment, a payer or application 250 can be notified by the EHR Blockchain API 275 of a new transaction 280, such as a prescription transaction. The notifications generated by the EHR Blockchain API 275 can include e-mails, texts, software alerts, and other suitable notifications. The notifications can be sent over the network 130. In another exemplary embodiment, the payer 250 can retrieve the SPPID 224 from the blockchain prescription transaction 280, send the SPPID 224 to the EHR Data API 110 to retrieve the specific patient's insurance data, and determine the patient's eligibility for the prescription, via eligibility analysis module 118, or other suitable software. The payer can retrieve any available EHR information for the specific patient (including name, address, birthday, social security number, account information, group ID, subscriber ID, pre-existing conditions, prescription history, etc.) through the EHR Data API 110, to determine whether the specific patient is eligible to have the prescription filled. In another exemplary embodiment, a patient's health insurance information can be correlated with information from the record 232 to determine whether the drug, product, or service is covered. In another exemplary embodiment, the payer 250 can be informed that the patient can't metabolize the generic drug, which can be on the payer formulary. The payer 250 can write an eligibility record 252 to the blockchain prescription transaction 280, through the EHR Blockchain API 275, indicating the eligibility. The eligibility record 252 can be a smart contract that executes, given certain conditions, to effect a specific outcome, such as indication of eligibility.

In one exemplary embodiment, a central fill facility provider or application 254 can be notified by the EHR Blockchain API 275 of a new transaction 280, such as a prescription transaction. The central fill facility provider 254 can retrieve the prescription information from the blockchain prescription transaction 280 to determine whether the prescription is available in a central fill facility and offer fulfillment option information. The central fill facility provider 254 can write a fulfillment option record 256 to the blockchain prescription transaction 280, through the EHR Blockchain API 275, indicating any fulfillment options available to the patient related to the prescription. Additionally, this fulfillment option record 256 can be a smart contract that executes, given certain conditions, to effect a specific outcome, such as selection of a delivery option. Smart contracts can execute automatically given received patient information (e.g., preferences or legal requirements, etc.), or can prompt the patient to make a selection via a user device 210. Additionally, smart contracts can require input from one or more sources to execute.

In one exemplary embodiment, the prescription can be finalized once the fulfillment option has been determined, such that the patient can go to a pharmacy to fill the prescription. The pharmacy provider or application 258 can be notified by the EHR Blockchain API 275 of a new transaction 280, such as a prescription transaction. The pharmacy provider 258 can retrieve the prescription information from the blockchain prescription transaction 280 to select the drug, the NDC the pharmacy wants to dispense from, or the drug price, among other selections. In another exemplary embodiment, the pharmacy provider 258 can write a modified prescription record 260 to the blockchain prescription transaction 280, through the EHR Blockchain API 275, indicating the selected drug, the NDC, and the drug price, related to the prescription. Additionally, this record 260 can be a smart contract that executes, given certain conditions, to effect a specific outcome, such as selection of the drug, the NDC, and the drug price.

In one exemplary embodiment, a pricing edit provider or application 262 can be notified by the EHR Blockchain API 275 of a new or modified transaction 280, such as a prescription transaction. The pricing edit provider 262 can retrieve the prescription information from the blockchain prescription transaction 280 to determine whether the drug pricing is correct. Traditionally, the pricing edits do not occur until the patient attempts to pay for the drug. In another exemplary embodiment, the central fill facility provider 262 can write a pricing record 264 to the blockchain prescription transaction 280, through the EHR Blockchain API 275, resolving any pricing issues related to the prescription. In another exemplary embodiment, the record 264 can be a smart contract that executes, given certain conditions, to effect a specific outcome, such as repricing of the drug. The SPPID 224 can be stored along with the record 266.

In one exemplary embodiment, after receiving the pricing edit 260, the pharmacy provider 258 can accept the repricing of the drug. The pharmacy provider 258 can write a final pricing record 266 to the blockchain prescription transaction 280, through the EHR Data Blockchain API 275, indicating the drug and setting the final price of the drug for fulfillment of the prescription. Additionally, this record 266 can be a smart contract that executes, given certain conditions, to reprice the drug.

In one exemplary embodiment, the payer or application 250 can be notified by the EHR Blockchain API 275 of a new or modified transaction 280, such as a prescription transaction. The payer can retrieve the prescription information from the blockchain prescription transaction 280 to determine the price it is authorized to pay. The payer 250 can write a payment price record to the blockchain prescription transaction, through the EHR Blockchain API 275, the price it will pay for the prescription fulfillment. Additionally, this record can be a smart contract that executes, given certain conditions, to effect a specific outcome, such as indicating the drug and the payment price amount.

In one exemplary embodiment, the pharmacy provider or application 258 can be notified by the EHR Blockchain API 275 of a new or modified transaction 280, such as a prescription transaction. The pharmacy provider can retrieve the prescription information from the blockchain prescription transaction 280 to indicate the final payment from the payer for the prescription fulfillment. The pharmacy provider can write a price paid record 268 to the blockchain prescription transaction, through the EHR blockchain API, indicating the drug and final price paid. Additionally, this record can be a smart contract that executes, given certain conditions, to effect a specific outcome, such as indicating the final payment amount paid. The SPPID 224 can be stored along with the record 268.

In one exemplary embodiment, once the pharmacy provider has indicated the final amount, the drug can be delivered to the patient. Additional functionality can occur once the drug has been delivered, such as the writing of a close record, payment of incentives, the awarding of points, or other suitable functions. In another exemplary embodiment, a drug manufacturer can provide an incentive 272 for a particular drug to be dispensed. The incentive 272 can be distributed to the patient via a digital currency, award account, or other suitable mechanism. In another exemplary embodiment, the pharmacy provider 258 can pay the clinical edit provider 242 for genomic/multiomic information 228 related to the prescription transaction 280 identifying that a patient cannot metabolize a particular drug. The payment 272 can be distributed to the clinical edit provider 242 via a digital currency, account, or other suitable mechanism. In another exemplary embodiment, the pharmacy provider 258 can pay the pricing edit provider 262 for pricing information related to the prescription transaction 280 for the particular drug. The payment 272 can be distributed to the clinical edit provider 242 via a digital currency, account, or other suitable mechanism. In another exemplary embodiment, the payer 250 can pay the pharmacy provider 258 for the fulfillment of the prescription. The payment 272 can be distributed to the clinical edit provider via a digital currency, account, or other suitable mechanism.

In one exemplary embodiment, each entity that accesses the EHR Data Blockchain 125 can view the contents of each record on the blockchain 125. In another embodiment, read access to the contents of each record on the blockchain 125 can be limited or denied.

In one exemplary embodiment, a Utility Token called EHRCash™, and a smart contract platform can be used to streamline payments between stakeholders and patients, eliminating the need for accounts receivable and accounts payable systems. EHRCash™ can exist in multiple forms, but a specific form can be used for a specific transaction. In another exemplary embodiment, EHRCash™ can be native to an underlying payment blockchain (BSV) or based on a FIAT Stable coin (e.g., USD, EUR, GBP, etc). In another exemplary embodiment, the token can:

Facilitate monetary rewards to patients for watching patient educational videos, reading educational blogs, and permissioned utilization of their data;

Facilitate payment of prescriptions and copays for insurance prescriptions;

Facilitate monetary rewards to pharmacies for the permissioned utilization of their data; and Facilitate payments from payers.

Patient Portal

In one exemplary embodiment, a patient portal can be provided by the server 102. The patient portal can be accessed by a user interface or a Patient Portal API. The patient portal can be achieved with software, hardware, an application programming interface (API), a network connection, a network transfer protocol, HTML, DHTML, JavaScript, Dojo, Ruby, Rails, other suitable applications, or suitable combinations thereof. In another exemplary embodiment, the patient portal can allow patients to:

Communicate with:
  Physicians
  Pharmacies
  Delivery Services
  Other Patients
  Etc.

View, add, modify, and delete their own medical information.

View their medication history

Connect, and configure Mobile Medical Applications (MMA's) and devices

Connect, and configure Mobile Fitness Applications (MFA's) and devices

Connect, and configure Internet of Things (IOT) applications and devices

View historical data from connected applications and devices

View historical data collected from real-time ambulance equipment.

View their EHRCash™ account balance.

Manage their EHRCash™ tokens.

Add, modify and delete permissions associated with granting access to their data.

In another exemplary embodiment, from the portal, users can review their pharmacy and clinical data, ask their pharmacist questions, engage in therapy sessions, or request prescription refills. Additionally, users can request clinical appointments, pre-enter data for immunizations, search for pharmacies having particular offerings, select MMA Permissions, and use EHRCash™.

MMA Permissions

In one exemplary embodiment, once logged into the EHR Patient Portal, a patient can revise their data sharing options called MMA Permissions. In another exemplary embodiment, by enabling their data to be shared with third parties, patients can enroll their account in the EHRCash™ program where each time the patient's data is shared, a portion of the program funding going to the patient.

EHRCash

In one exemplary embodiment, EHRCash™ can be offered to patients through data sharing at the EHR Patient Portal. EHRCash™ can be a tokenized digital currency that the patient can redeem through several different channels including gift cards, prescription purchases, health spending accounts, online purchases, and other suitable mediums.

Wearables Use Case

In one exemplary embodiment, by integrating the systems described herein, a patient can receive a wearable device in exchange for their participation in a manufacturer-sponsored data-sharing program. The data collected through the wearable device can be added to the patient's EHR, which can make it available for future sharing opportunities. In another exemplary embodiment, step count, heart rates, blood pressures, activity, sleep cycles, etc., can be added as measured results through the system. With each additional monitoring system, a more complete EHR for the patient can be created, thus becoming a more valuable sharing tool.

Profile Rating

In one exemplary embodiment, patient profiles can be categorized by completeness and quantity of data. By adding LABs, prescriptions, clinical opportunities, etc. to the patient's profile, it becomes a more complete and valuable record for manufacturers. In another exemplary embodiment, a higher-rated profile can earn a patient more EHR-Cash™ each time it is shared.

Physician Portal

In one exemplary embodiment, a physician portal can be achieved with software, hardware, an application programming interface (API), a network connection, a network transfer protocol, HTML, DHTML, JavaScript, Dojo, Ruby, Rails, other suitable applications, or suitable combinations thereof. In another exemplary embodiment, the physician portal can allow physicians to:

Manage demographic information
Manage legal information
Manage accreditation references
Manage digital identity references
Manage contact information
Connect with their Patients, to:
    Communicate about medical information, issues, complications, etc.
    Review a patients' medical history.
    Review current medications from a variety of prescribers.
    Review data collected from medical, fitness and IOT devices.
Communicate with pharmacies to:
    Review prescription edit outcomes
    Authorize additional refills for a prescription
    Change medications
    Stop medications
View their EHRCash™ account balance.
Manage their EHRCash™ tokens.

Drug Manufacturer Portal

In one exemplary embodiment, a drug manufacturer portal can be achieved with software, hardware, an application programming interface (API), a network connection, a network transfer protocol, HTML, DHTML, JavaScript, Dojo, Ruby, Rails, other suitable applications, or suitable combinations thereof. In another exemplary embodiment, a drug manufacturer portal can allow a drug manufacturer to:

Manage demographic information
Manage legal information
Manage contact information
Request a wide variety of data reports for a specific list of drugs and associated data collected by medical devices.
Request a wide variety of analytical reports
Manage Educational Videos
Manage reward amounts, and parameters associated with educational videos
View their EHRCash™ account balance.
Manage their EHRCash™ tokens.

Pharmacy Portal

In one exemplary embodiment, a pharmacy portal can be achieved with software, hardware, an application programming interface (API), a network connection, a network transfer protocol, HTML, DHTML, JavaScript, Dojo, Ruby, Rails, other suitable applications, or suitable combinations thereof. In another exemplary embodiment, a pharmacy portal can allow pharmacies to:

Manage demographic information
Manage legal information
Manage accreditation references
Manage digital identity references
Manage contact information
Manage Financial, Clinical and Multi-omics edits, by:
    Selecting edits to be executed
    Defining and loading qualification rules for selected edits
View their EHRCash™ account balance.
Manage their EHRCash™ tokens.
Select Central Fill Providers
Select Prescription Delivery Providers
Select Inventory Management Providers Authentication In one exemplary embodiment, the EHR Data Blockchain system 200 can provide a "password-less" experience for users when logging into the Pharmacy, Physician, Patient, and Drug Manufacturer portals, including standards such as the FIDO2 standard, among others.

Security—FIDO2 cryptographic login credentials can be unique across every website, never leave the user's device, and never stored on a server. This security model eliminates the risks of phishing, all forms of password theft, and replay attacks.

Convenience—Users can unlock cryptographic login credentials with simple built-in methods such as fingerprint readers or cameras on their devices, or by leveraging easy-to-use FIDO security keys. Consumers can select the device that best fits their needs.

Privacy—Because FIDO cryptographic keys can be unique for each Internet site, they cannot be used to track users across sites. Plus, biometric data, when used, never leaves the user's device.

Scalability—Websites can enable FIDO2 through a simple JavaScript API call that is supported across leading browsers and platforms on billions of devices consumers use every day.

Digital Identities

In one exemplary embodiment, digital identities can be implemented by the system for public facing components of the Physician, Pharmacy, and Patient portals. For example, a Physician's digital identity can be exposed when interacting on social media. These identities can be interoperable across administrative domains, applications, and any other organizational silo.

Digital Accreditations

In one exemplary embodiment, accreditation can be implemented by the system 100 for the public-facing components of the Physician, Pharmacy, and Patient portals. For example, a Physician can reference their accreditations within the Physician portal, which can be used to: support their digital identity, attract new business, prove accreditation when interacting on our social media platform, and other relevant uses.

Privacy

In one exemplary embodiment, prescriptions, prescription transactions, and medical data recorded to the blockchain 125 contain no direct reference to the patient, physician or pharmacy entity. Single-use public ID's, which are generated from the private IDs of the entity using one-way cryptographic techniques, can obfuscate the actual identity of the entities. This technique can allow the holder of the private ID the ability to link their identity for reporting purposes. In another exemplary embodiment, all data can be stored on the blockchain as a graph/hierarchy structure. Each node can contain specific information (e.g., patient name, address, medication, etc.) in the graph/heirarchy that can be encrypted with its own encryption key. This graph/heirarchy structure may not be visible on the blockchain and thereby provide an obfuscation of the data structure. In another exemplary embodiment, only the master private key for the patient/user can understand the structure.

Private Patient Record

In one exemplary embodiment, the patient's private ID is never revealed and can be used to identify the patient's medical record. The patient's medical record can contain information such as:

Last Name
   Middle Name
   First Name
   Nicknames
   Birthdate.
   Gender
   Addresses composed of:
       Address Line
       City
       State
       Postal Code
   Mobile Phone Numbers
   Land Line Numbers
   Insurance ID's
   Medical History
   Diagnosis
   Medications
   Treatment Plans.
   Immunization Dates
   Allergies
   Multiomics Data
   Laboratory Tests
   Laboratory Results.
   Radiology Images
   Mobile Medical Application Data
   Mobile Fitness Application Data
   Medical Device Data
   Fitness Device Data.
   Internet of Things Device Data
   Among others.

Private Physician Record

In one exemplary embodiment, a physician's private and public keys can be generated using the BIP-0032 algorithm.

The physician's private key is not revealed and can be used to identify the physician's information. The physician's information can include:

Last Name
   Middle Name
   First Name
   Nicknames
   Birthdate
   Gender
   Addresses composed of:
       Address Line
       City
       State
       Postal Code
   Mobile Phone Numbers
   Land Line Numbers
   Specialties
   License Numbers
   Credentials
   Other relevant information Private Pharmacy Record In one exemplary embodiment, the pharmacy's private key is never exposed and is used to identify the pharmacy details. The pharmacy details can contain information such as:

Name
   Chain Code
   Address composed of:
       Address Line
       City
       State
       Postal Code
   Mobile Phone Numbers
   Land Line Numbers
   Services
   License Numbers
   Identification Numbers Granting Permissions In one exemplary embodiment, each entity can have a portal which can allow the entity to grant permission to a third party to use a specific data item or range of data items contained in the blockchain. In another exemplary embodiment, an 'Authorization Token' (e.g., authToken) can be created on behalf of the user/entity, after the user/entity has granted permission for read and/or write access to specific data elements of their EHR Data. For example, the 'authToken' can have a specific lifespan (or Time To Live) and can only be renewed with authorization from the user/entity. In another exemplary embodiment, the governing body of the portal, government (e.g., region, national, etc.), and law enforcement can be granted privileges that can allow them to retrieve the details of the entities. Once revealed those details must be protected to the extent of the associated government regulations (e.g., HIPPA). An entities private key may never be revealed.

In another exemplary embodiment, a drug manufacturer can request deidentified data for as many patients as possible between a specific date range. The data requested can include: prescription-transaction data for a specific NDC, patient medical details, and specific mobile medical application data. When the utility receives this request, it can implement the following:

Retrieve all the transactions that match the drug code.
   Determine the entities associated with the transactions.
   Determine if the entity has a default or specific permission for the specific types of data being requested. If not, the entity will be contacted and the permission requested.

Once all permissions have been determined the result set will be returned to the drug manufacturer.

Data Queries

In one exemplary embodiment, data queries can be used by any member of the blockchain. A request to query the blockchain can include the following:

Requestor ID

Requestor Usage (Financial, Research, etc.)

Request Description

Request Type

Request Data Types

Data Fields

Request Date Range

Request Rewards.

The predefined Request Type selected can dictate:

the data types (prescription, prescription transaction, medical device data, etc.)

the desired fields within each data type.

In another exemplary embodiment, the data returned by the query can be filtered based on permissions granted by the associated patients, and the selection criteria specified by the Request Type.

The present disclosure achieves at least the following advantages:

1. improves the performance of traditional systems by utilizing the EHR patient transaction blockchain as a workflow space to process a transaction until the transaction completes, is signed, and is distributed for consensus.

2. implements smart contracts to determine and define workflow processes, drug interactions, fulfillment, expected outcomes, triggering events, and pricing, among other data elements;

3. reduces the utilization of additional processing resources and network utilization from computationally-expensive data storage, data bottlenecks, and system queries;

4. generates an immutable record of the transaction for subsequent review and auditing;

5. provides a platform for providing easy and efficacious prescription editing, processing, and payment, leveraging cryptocurrencies and APIs to facilitate transactions; and 6. accesses and retrieves patient identifiable information (PII) and generates a non-patient-identifiable Single Purpose Patient ID (SPPID) for a particular patient for use in a discrete transaction.

Persons skilled in the art will readily understand that these advantages (as well as the advantages indicated in the summary) and objectives of this system would not be possible without the particular combination of computer hardware and other structural components and mechanisms assembled in this inventive system and described herein. It will be further understood that a variety of programming tools, known to persons skilled in the art, are available for implementing the control of the features and operations described in the foregoing material. Moreover, the particular choice of programming tool(s) may be governed by the specific objectives and constraints placed on the implementation plan selected for realizing the concepts set forth herein and in the appended claims. In particular, the integration of commercial-off-the-shelf (COTS) equipment may be utilized in the new and unconventional manner described herein to achieve one or more aspects of the claims.

The description contained herein should not be read as implying that any particular element, step, or function can be an essential or critical element that must be included in the claim scope. Also, none of the claims are intended to invoke 35 U.S.C. § 112(f) with respect to any of the appended claims or claim elements unless the exact words "means for" or "step for" are explicitly used in the particular claim, followed by a recited function. Use of terms including, but not limited to, "mechanism," "module," "device," "unit," "component," "element," "member," "apparatus," "machine," "system," "processor," "processing device," or "controller" within a claim can be understood and intended to refer to structures known to those skilled in the relevant art, as further modified or enhanced by the features of the claims themselves, and are not intended to invoke 35 U.S.C. § 112(f).

The disclosure may be embodied in other specific forms without departing from the spirit or essential characteristics thereof. For example, each of the new structures described herein, may be modified to suit particular local variations or requirements while retaining their basic configurations or structural relationships with each other or while performing the same or similar functions described herein. The present embodiments are therefore to be considered in all respects as illustrative and not restrictive. Accordingly, the scope of the inventions are established by the appended claims rather than by the foregoing description. All changes which come within the meaning and range of equivalency of the claims are therefore intended to be embraced therein. Further, the individual elements of the claims are not well-understood, routine, or conventional. Instead, the claims are directed to the unconventional inventive concept described in the specification.

What is claimed is:

1. An electronic record data blockchain system configured to process a transaction, comprising:

one or more computer-readable storage media configured to store a blockchain; and one or more processors programmed to execute computer program instructions that, when executed, cause the computer system to:

receive a query related to a user, the query including identifying information associated with the user;

generate, in response to a determination that a current record exists for the user, a first single-purpose ID for a user, wherein the first single-purpose ID enables a blockchain system to use the first single-purpose ID instead of the user identifying information;

receive a first electronic prescription;

initiate a first transaction on the blockchain using the first single-purpose ID, the first electronic prescription, and no user-identifying information;

automatically receive preferences or legal requirements related to the user;

implement a smart contract configured to define workflow processes, triggering events, or pricing based on the automatically received preferences or legal requirements related to the user, and write an edit record to the blockchain;

generate and write a close record to the blockchain including output from the smart contract;

based on the output from the smart contract, initiate one or more digital currency transactions related to the first transaction once the close record has been written to the blockchain; and abandon use of the first single-purpose ID after the close record has been written to the blockchain, wherein abandoning the use of the first single-purpose ID after the close record has been written to the blockchain prevents exposure of information from a subsequent transaction associated with another single-purpose ID, such that any potential compromise of the first single-purpose ID compromises information from the first transaction and not the subsequent transaction.

2. The electronic record data blockchain system of claim 1, wherein the smart contract is used to streamline payments between stakeholders and the user.

3. The electronic record data blockchain system of claim 1, wherein the smart contract determines the final payment amount paid based on certain conditions.

4. The electronic record data blockchain system of claim 1, wherein the smart contract prompts the user to make a selection via a user device.

5. The electronic record data blockchain system of claim 1, wherein the blockchain system mitigates data discrepancies for electronic patient data.

6. The electronic record data blockchain system of claim 1, wherein once the first transaction is completed, the first single-purpose ID can only be used to read information associated with the first transaction from the blockchain.

7. A method of processing a blockchain transaction, the method implemented by a server system comprising one or more processors executing computer program instructions that, when executed, perform the method, comprising:

receiving a query related to a user, the query including identifying information associated with the user;

generating, in response to a determination that a current record exists for the user, a first single-purpose ID for a user, wherein the first single-purpose ID enables a blockchain system to use the first single-purpose ID instead of the user identifying information;

receiving a first electronic prescription;

initiating a first transaction on the blockchain using the first single-purpose ID, the first electronic prescription, and no user-identifying information;

automatically receiving preferences or legal requirements related to the user;

implementing a smart contract configured to define workflow processes, triggering events, or pricing, based on the automatically received preferences or legal requirements related to the user, and write an edit record to the blockchain;

generating and writing a close record to the blockchain including output from the smart contract;

based on the output from the smart contract, initiating one or more digital currency transactions related to the first transaction once the close record has been written to the blockchain;

abandoning use of the first single-purpose ID after the close record has been written to the blockchain, wherein abandoning the use of the first single-purpose ID after the close record has been written to the blockchain prevents exposure of information from a subsequent transaction associated with another single-purpose ID, such that any potential compromise of the first single-purpose ID compromises information from the first transaction and not the subsequent transaction.

8. The method of claim 7, wherein the smart contract is used to streamline payments between stakeholders and the user.

9. The method of claim 7, wherein the smart contract determines the final payment amount paid based on certain conditions.

10. The method of claim 7, wherein the smart contract prompts the user to make a selection via a user device.

11. The method of claim 7, wherein the blockchain system mitigates data discrepancies for electronic patient data.

12. The method of claim 7, wherein once the first transaction is completed, the first single-purpose ID can only be used to read information associated with the first transaction from the blockchain.

* * * * *